United States Patent [19]

Law

[11] Patent Number: 4,822,511
[45] Date of Patent: Apr. 18, 1989

[54] PRESERVATIVE COMPOSITIONS COMPRISING A SYNERGISTIC MIXTURE OF ISOTHIAGOLONES

[75] Inventor: Andrew B. Law, Newtown, Pa.

[73] Assignee: Rohm and Haas Company, Philadelphia, Pa.

[21] Appl. No.: 190,864

[22] Filed: May 6, 1988

[51] Int. Cl.$^4$ .............................................. C11D 3/48
[52] U.S. Cl. .................................. 252/106; 106/18.33; 210/764; 252/107; 422/28; 422/37; 424/70; 514/372; 523/122
[58] Field of Search ...................... 252/106, 107, 47.5, 252/DIG. 13, 5; 514/372; 106/18.33; 424/70; 210/764; 422/28, 37; 523/122

[56] References Cited

U.S. PATENT DOCUMENTS

| | | | |
|---|---|---|---|
| 4,067,878 | 1/1978 | Miller et al. | 548/101 |
| 4,105,431 | 8/1978 | Lewis et al. | 252/106 |
| 4,173,643 | 11/1979 | Law | 514/372 |
| 4,252,694 | 2/1981 | Lewis et al. | 252/106 |
| 4,295,932 | 10/1981 | Pocius | 162/161 |
| 4,608,183 | 8/1986 | Rossmoore | 252/36 |
| 4,655,936 | 4/1987 | Stuebner | 210/764 |
| 4,661,503 | 4/1978 | Martin et al. | 514/372 |
| 4,732,905 | 3/1988 | Donofrio et al. | 514/372 |

*Primary Examiner*—Prince E. Willis
*Attorney, Agent, or Firm*—Terence P. Strobaugh

[57] ABSTRACT

A composition comprising 2-n-octyl isothiazolone 5-chloro-2-methyl-4-isothiazolin-3-one and 2-methyl-4-isothiazolin-3-one has been found to provide superior preservative performance as compared to the individual components.

7 Claims, No Drawings

PRESERVATIVE COMPOSITIONS COMPRISING A SYNERGISTIC MIXTURE OF ISOTHIAGOLONES

BACKGROUND OF THE INVENTION

The invention relates to the preservation of aqueous products such as liquid dishwash detergents, surfactants, and liquid soaps against microbial degradation. More specifically, the invention relates to the use of compositions comprising 2-n-octylisothiazolin-3-one, 5-chloro-2-methyl-4-isothiazolin-3-one and 2-methyl-4-isothiazolin-3-one for the preservation of materials susceptible to microbial degradation.

Materials containing organic material in aqueous solutions may be highly susceptible to attack from microorganisms. Materials such as liquid dishwash detergents, surfactants, liquid soaps, adhesives, metal working fluids, hand cleaners, paints, mineral slurries, polymer emulsions and shampoos are routinely formulated with antimicrobial agents to prevent the growth of putrifying microorganisms.

Numerous materials are known in the literature for use in preventing microbial growth in susceptible materials. Some example are found in U.S. Pat. Nos. 4,105,431 and 4,135,945 and in 4,725,611.

SUMMARY OF THE INVENTION

This invention relates to the discovery that a combination of isothiazolones when used at extremely low amounts is more effective than any of the components at similar dosage rates.

DESCRIPTION OF THE PREFERRED EMBODIMENT

The preferred embodiment of this invention comprises:

a. Component 1: comprises a mixture of 75% 5-chloro-2-methyl-4-isothiazolin-3-one and 25% 2-methyl-4-isothiazolin-3-one; and b. Component 2: 2-n octyl-4-isothiazolin-3-one.

These two components may be mixed in a range of ratios from 1 part Component 1: 10 parts Component 2 to 10 parts Component 1: 1 part Component 2. The most preferred ratio is in the range 2 parts Component 1: 1 part Component 2 to 5 part Component 1: 1 part Component 2. Typical use levels are in the range of 1 to 15 ppm of Component 1 plus Component 2 as the active ingredient with preferred use levels in the range of from 1 to 4 ppm of the compositions.

EXAMPLES

The following experiments demonstrate the invention.

Various levels of the two components are added to a liquid dish detergent formulation. The test samples are inoculated with bacteria that has been previously shown to be able to degrade the liquid dish detergent. Additional microbial inoculum is added to the samples every week for four weeks. The level of microbial growth present in the samples is determined each week. Standard plate counting techniques are employed using trypticase soy agar and rose bengal chloramphenicol agar plates. Samples are evaluated to determine the number of weeks that the samples remained free of microbial growth. Any growth in these products is not acceptable and is judged a failure.

MIC Component 1

Component 1 is known to have a broad spectrum of antimicrobial activity. Minimum inhibitory concentrations (MIC) of Component 1 for various types of microorganisms appear in Table 1:

TABLE 1

|  | MIC (ppm active ingredient) |
|---|---|
| Gram Positive Bacteria | 2.0–9.0 |
| Gram Negative Bacteria | 2.0–9.0 |
| Fungi | 2.0–9.0 |

MIC Component 2

Component 2 is known to be effective in the control of fungi but is much less effective in the control of bacteria, particularly gram negative bacteria. Minimum inhibitory concentrations for various types of microorganisms appear in Table 2.

TABLE 2

|  | MIC (ppm active ingredient) |
|---|---|
| Gram Positive Bacteria | 8.0–32.0 |
| Gram Negative Bacteria | 125.0–1000.0 |
| Fungi | 0.6–16.0 |

By itself Component 2 is not effective in preventing microbial growth in a susceptible material which typically becomes contaminated with fungi and bacteria, particularly gram negative bacteria. Component 1 is known to be effective at a dosage level of at least 4 ppm. A mixture of Component 1 and Component 2 has been found, however, to be more effective than would be predicted based on the spectrum of activities of the two separate components.

Table 3 shows results of a comparative test in a liquid dishwashing detergent. (Weeks until the onset of microbial growth is presented as a function of concentration of the two components.)

TABLE 3

| | Comparison of Activities | | |
|---|---|---|---|
| Concentration of Component 1 (ppm active) | Concentration of Component 2 (ppm active) | Total Active Ingredient | Weeks Until Failure |
| 1.0 | 0 | 1.0 | 0 |
| 2.0 | 0 | 2.0 | 0 |
| 4.0 | 0 | 4.0 | >4 |
| 1.0 | 0.2 | 1.2 | 4 |
| 1.0 | 0.5 | 1.5 | 4 |
| 2.0 | 0.4 | 2.4 | >4 |
| 2.0 | 1.0 | 3.0 | >4 |

What is claimed:

1. A composition comprising a mixture of 75% 5-chloro-2-methyl-4-isothiazolin-3-one and 25% 2-methyl-4-isothiazolin-3-one (Component 1) and 2-n-octyl isothiazolin-3-one (Component 2) in a ratio of Component 1 to Component 2 of between about 1:10 and about 10:1.

2. The composition of claim 1 wherein the ratio of Component 1 to Component 2 is between about 5:1 and about 2:1.

3. A method for controlling microbial degradation of organic material in aqueous solution which comprises adding an effective amount of the composition of claim 1.

4. A method for controlling microbial degradation of organic material in aqueous solution which comprises adding an effective. amount of the composition of claim 2.

5. The method of claim 4 wherein the effective amount is from 1 to 15 ppm of the composition.

6. The method of claim 4 wherein the effective amount is from 1 to 3 ppm of the composition.

7. The method of claim 3 wherein the aqueous solution is selected from a liquid dishwash detergent surfactants, liquid soaps, adhesives, metal working fluid, hand cleaners, paint, mineral slurries, polymer emulsions and shampoo.

* * * * *

UNITED STATES PATENT AND TRADEMARK OFFICE
CERTIFICATE OF CORRECTION

PATENT NO. : 4,822,511

DATED : April 18, 1989

INVENTOR(S) : Andrew B. Law

It is certified that error appears in the above-identified patent and that said Letters Patent is hereby corrected as shown below:

On the title page, item [54], and in column 1, line 4,
In the title the word "ISOTHIAGOLONES" should read -- ISOTHIAZOLONES --.

Signed and Sealed this

Ninth Day of January, 1990

*Attest:*

JEFFREY M. SAMUELS

*Attesting Officer*     *Acting Commissioner of Patents and Trademarks*